United States Patent [19]

Oharu et al.

[11] Patent Number: 5,557,017
[45] Date of Patent: Sep. 17, 1996

[54] METHOD FOR PRODUCING A HYDROFLUOROCARBON

[75] Inventors: Kazuya Oharu; Ryuji Seki; Seisaku Kumai, all of Yokohama, Japan

[73] Assignee: Asahi Glass Company Ltd., Tokyo, Japan

[21] Appl. No.: 318,258

[22] Filed: Oct. 5, 1994

[30] Foreign Application Priority Data

| Oct. 5, 1993 | [JP] | Japan | 5-249312 |
| Oct. 14, 1993 | [JP] | Japan | 5-257236 |
| Nov. 5, 1993 | [JP] | Japan | 5-276815 |
| Apr. 6, 1994 | [JP] | Japan | 6-068541 |

[51] Int. Cl.$^6$ ................................................. C07C 19/08
[52] U.S. Cl. ......................................................... 570/176
[58] Field of Search ............................................. 570/176

[56] References Cited

FOREIGN PATENT DOCUMENTS

| 0308923 | 3/1989 | European Pat. Off. . |
| 0499516 | 8/1992 | European Pat. Off. . |
| 2116524 | 7/1972 | France . |

*Primary Examiner*—Alan Siegel
*Attorney, Agent, or Firm*—Oblon, Spivak, McClelland, Maier, & Neustadt, P.C.

[57] ABSTRACT

A method for producing a hydrofluorocarbon of the formula a $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with an alkali metal hydroxide under action of an alcohol mixture comprising a primary alcohol and a secondary alcohol.

14 Claims, No Drawings

METHOD FOR PRODUCING A HYDROFLUOROCARBON

The present invention relates to a method for producing a hydrofluorocarbon.

A hydrofluorocarbon is a substitute for a chlorofluorocarbon compound such as 1,1,2-trichloro-1,2,2-trifluoroethane, and it is a compound which does not destroy the ozone layer.

The following reports have been made with respect to methods for preparing a hydrofluorocarbon using an iodofluorocarbon as a starting material.

(1) A method of conducting the reduction in the presence of zinc (J. Fluorine Chem., 6,297, 1975).

(2) A method for the synthesis by a reaction employing the Grignard reagent (J. Fluorine Chem., 3,247, 1973).

(3) A method for the synthesis by a liquid phase reduction by employing hydrogen and a Raney nickel catalyst (Ger. Offen. 2,060,041,J. Fluorine Chem. Soc., 3761, 1953).

(4) A method for the synthesis by a reduction employing sodium hypophosphite or a palladium or a platinum catalyst (J. Fluorine Chem., 55,101, 1991).

(5) A method for reacting the starting material with alcoholic potassium hydroxide (J. Chem. Soc., 3761, 1953).

(6) A method of reacting the starting material with an alkali metal hydroxide in methanol (EP 0,449,516 A1).

The method (1) has problems with respect to the handling and disposal of zinc and a zinc slurry resulting from the reaction.

The method (2) has a possible danger such that the Grignard reagent is ignitable by moisture or the like. Further, it has a high possibility of danger, since a low boiling point ether-type solvent is used. It further has a problem with respect to disposal of the liquid waste.

The method (3) has a high possibility of danger, since the reaction is required to be conducted under high temperature and high pressure conditions i.e. at 65° C. under from 60 to 80 atm.

The method (4) has a problem that it requires an expensive catalyst.

The method (5) has problems that a high temperature of from 100° to 130° C. is required for the reaction, and the yield is low.

With the method (6) employing methanol and an alkali metal hydroxide, it is difficult to bring the conversion of the iodofluorocarbon as a starting material to an industrially satisfactory level, and it is also difficult to obtain a hydrofluorocarbon with a high purity.

Further, if an aqueous solution of an inexpensive alkali metal hydroxide which is commonly used for an industrial purpose, is employed as the alkali metal hydroxide, the conversion will further deteriorate. Furthermore, since the alkali metal hydroxide contains water, or since water is formed by the reaction, the water content in the reaction system tends to be substantial, and the reaction system will be separated into two layers i.e. a fluorocarbon layer and an aqueous methanol layer, whereby reproducibility of the yield is likely to be low depending upon the stirring condition, etc.

Further, in (6), a reaction employing isopropyl alcohol and an alkali metal hydroxide, is also disclosed, but both of the conversion and the selectivity are low, and the yield is also low at a level of 22.6%. Further, there is a problem that by-products of the reaction are likely to undergo a side reaction such as an aldol condensation in the presence of an alkali metal hydroxide, to form a tar-like substance.

Further, there has been a problem that if a hydrofluorocarbon prepared by using only methanol or isopropyl alcohol as the solvent, is used directly as a solvent for polymerization without purification by distillation, the desired polymerization does not proceed, or the polymer tends to be colored.

The present inventors have conducted extensive studies on a method for efficiently producing a hydrofluorocarbon using an iodofluorocarbon as a starting material. As a result, they have found it possible to obtain a highly pure hydrofluorocarbon safely at a high conversion and a high selectivity, by reacting an iodofluorocarbon under action of an alcohol mixture comprising a primary alcohol and a secondary alcohol.

Thus, the present invention provides a method for producing a hydrofluorocarbon of the formula a $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with an alkali metal hydroxide under action of an alcohol mixture comprising a primary alcohol and a secondary alcohol.

Now, the present invention will be described in detail with reference to the preferred embodiments.

The iodofluorocarbon used as a starting material of the present invention is a compound of the formula $I_nR_fI$, wherein n is 0 or 1, and when n is 0, $R_f$ is a $C_{2-12}$ linear or branched polyfluoroalkyl group, preferably a $C_{3-8}$ polyfluoroalkyl group, more preferably $CF_3CF_2CF_2CF_2CF_2CF_2-$, and when n is 1, $R_f$ is a $C_{2-12}$ linear or branched polyfluoroalkylene group, preferably a $C_{3-8}$ polyfluoroalkylene group, more preferably $-CF_2CF_2CF_2CF_2-$.

Specific examples of the iodofluorocarbon include 1-iodo-1,1,2,2,2-pentafluoroethane $ICF_2CF_3$, 1-iodo-1,1,2,2,3,3,4,4,4-nonafluorobutane $I(CF_2)_4F$, 1-iodo-1,1,2,2,3,3,4,4,5,5,6,6,6-tridecafluorohexane $I(CF_2)_6F$, 1-iodo-1,1,2,2,3,3,4,4,5,5,6,6,7,7,8,8,8-heptadecafluorooctane $I(CF_2)_8F$, 2-iodo-1,1,1,2,3,3,3-heptafluoropropane $CF_3CFICF_3$, 4-iodo-1,1,1,2,3,3,4,4-octafluoro-2-trifluoromethylbutane $(CF_3)_2CF(CF_2)_2I$, 6-iodo-1,1,1,2,3,3,4,4,5,5,6,6-dodecafluoro-2-trifluoromethylhexane $(CF_3)_2CF(CF_2)_4I$, 1,2-diiodo-1,1,2,2-tetrafluoroethane $I(CF_2)_2I$, 1,4-diiodo-1,1,2,2,3,3,4,4-octafluorobutane $I(CF_2)_4I$, and 1,6-diiodo-1,1,2,2,3,3,4,4,5,5,6,6-dodecafluorohexane $I(CF_2)_6I$. However, the iodofluorocarbon is not limited to such specific examples.

It is a feature of the present invention to react the above iodofluorocarbon with an alkali metal hydroxide under action of an alcohol mixture comprising a primary alcohol and a secondary alcohol.

Such a reaction which is not necessarily clearly understood, may be represented by the following formula.

$$I_nR_fI+(n+1)R^1R^2CHOH+(n+1)MOH \rightarrow H_nR_fH+(n+1)R^1R^2C=O+(n+1)MI+(n+1)H_2O \qquad (1)$$

In the formula (1), $R_f$ and n are as defined above, $R^1$ is hydrogen or an alkyl group, $R^2$ is an alkyl group, and M is an alkali metal atom.

The primary alcohol and the secondary alcohol are not particularly limited, and known or well known alcohols may be employed. Usually, as the primary alcohol, methanol, ethanol, propyl alcohol or butyl alcohol may, for example, be preferably employed. Particularly preferred is methanol for such reasons that the solubility of the alkali metal hydroxide is thereby high, its treatment after the reaction is easy, and it is inexpensive. As the secondary alcohol, isopropyl alcohol or isobutyl alcohol may, for example, be preferably employed. Particularly preferred is isopropyl alcohol for such reasons that the conversion is thereby high, and it is inexpensive.

The ratio of the primary alcohol to the secondary alcohol is not particularly limited. However, in a usual case, the weight ratio of the primary alcohol to the secondary alcohol is preferably within a range of from 0.5:1 to 1000:1, more preferably from 1:1 to 200:1. If the proportion of the secondary alcohol becomes too large, it is likely that the formation of high boiling point compounds will be substantial. On the other hand, if the proportion of the secondary alcohol is too small, the reaction rate tends to be low.

The amount of the primary alcohol is usually preferably from 0.1 to 10 parts by weight per part by weight of the iodofluorocarbon as the starting material. The amount of the primary alcohol is preferably larger than the amount capable of completely dissolve the alkali metal hydroxide.

In a usual case, as the alkali metal hydroxide, sodium hydroxide or potassium hydroxide is preferred. In the present invention, the alkali metal hydroxide can be employed in the form of an aqueous solution. Accordingly, an inexpensive aqueous alkali metal hydroxide solution which is commercially available for industrial use, may be used as it is.

The amount of the alkali metal hydroxide is usually preferably at least 1.5 mols, preferably from 1.5 to 3 mols, per mol of the iodofluorocarbon as the starting material. If the alkali metal hydroxide is used in excess, the reaction rate will be high. Accordingly, the concentration is preferably as high as possible within a range that the alkali metal hydroxide can be dissolved in the reaction system.

The above reaction conditions may suitably be modified depending upon the types, amounts, etc. of the reactants and the alcohols. If the reaction temperature is too low, the reaction will hardly proceed, and if it is too high, such is dangerous, and accordingly, it is advisable to control the temperature to a level where the reaction solution is refluxed. Usually, the temperature is from 40° to 70° C. The reaction pressure may be atmospheric pressure, reduced pressure or elevated pressure, preferably atmospheric pressure. The reaction time is usually from 1 to 10 hours. The reaction may be conducted under pressure.

In the method of the present invention, a product of a high purity can be obtained by washing the crude reaction products with water. According to the method of the present invention, the conversion of the iodofluorocarbon as the starting material is very high. Accordingly, it is advantageous that the product can be used without purification by distillation, except for a special application where it is required to eliminate even a very small amount of an iodine compound at a level of a few ppm.

The hydrofluorocarbon to be formed by the above reaction is a compound of the formula $H_nR_fH$. In this formula, n is 0 or 1. When n is 0, $R_f$ is a $C_{2-12}$ linear or branched polyfluoroalkyl group, preferably a $C_{3-8}$ polyfluoroalkyl group, particularly preferably $CF_3CF_2CF_2CF_2CF_2CF_2$—. When n is 1, $R_f$ is a $C_{2-12}$ linear or branched polyfluoroalkylene group, preferably a $C_{3-8}$ polyfluoroalkylene group, particularly preferably —$CF_2CF_2CF_2CF_2$—.

Specific examples of the hydrofluorocarbon include 1,1,1,2,2-pentafluoroethane $F(CF_2)_2H$, 1,1,1,2,2,3,3,4,4-nonafluorobutane $F(CF_2)_4H$, 1,1,1,2,2,3,3,4,4,5,5,6,6-tridecafluorohexane $F(CF_2)_6H$, 1,1,1,2,2,3,3,4,4,5,5,6,6,7,7,8,8-heptadecafluorooctane $F(CF_2)_8H$, 1,1,2,3,3,3-heptafluoropropane $CF_3CFHCF_3$, 1,1,1,2,3,3,4,4-octafluoro-2-trifluoromethylbutane $(CF_3)_2CF(CF_2)_2H$, 1,1,1,2,3,3,4,4,5,5,6,6-dodecafluoro-2-trifluoromethylhexane $(CF_3)_2CF(CF_2)_4H$, 1,1,2,2-tetrafluoroethane $H(CF_2)_2H$, 1,1,2,2,3,3,4,4-octafluorobutane $H(CF_2)_4H$ and 1,1,2,2,3,3,4,4,5,5,6,6-dodecafluorohexane $H(CF_2)_6H$.

The above reaction may be carried out in the presence of a phase transfer catalyst. When a phase transfer catalyst is present, either one of the primary alcohol and the secondary alcohol may be used alone. However, from the viewpoint of the reaction performance, it is preferred to employ their mixture.

In the case where the phase transfer catalyst is used, the amount of the primary alcohol and the secondary alcohol is usually from 0.1 to 10 parts by weight, preferably from 0.2 to 2 parts by weight, per part by weight of the iodofluorocarbon as the starting material, either when they are used alone or when they are used in combination as their mixture. In the case where they are used in combination as their mixture, the respective proportions are not particularly limited, but in a usually case, the weight ratio of the primary alcohol to the secondary alcohol is preferably within a range of from 1000:1 to 0.5:1, more preferably within a range of from 100:1 to 1:1.

In the reaction of the present invention, water forms as a by-product of the reaction, as shown by the formula (1). Further, water is usually contained in the alkali metal hydroxide or in the primary alcohol or the secondary alcohol to be used for the reaction, and the amount of water is larger when reagents for industrial use are employed. Further, when an aqueous solution of an inexpensive alkali metal hydroxide for industrial use, is used as the alkali metal hydroxide, the amount of water contained in the reaction system, will further increase.

If the amount of water in the reaction system increases, the reaction system tends to separate into two layers, i.e. a hydrophobic layer containing the iodofluorocarbon starting material and the hydrofluorocarbon product, and a hydrophilic layer containing the primary alcohol, the secondary alcohol and water, whereby it is likely that the reaction rate lowers, and reproducibility of the reaction performance becomes low depending upon the stirring condition, etc. However, by the presence of the phase transfer catalyst in the reaction system, the reactivity and the reaction performance will not substantially decrease, even when the reaction system is separated into such two layers. The phase transfer catalyst serves not only to increase the reaction rate, the conversion and the selectivity but also to maintain reproducibility of a good reaction performance.

The phase transfer catalyst may, for example, be a quaternary ammonium salt such as tetramethyl ammonium chloride, tetraethyl ammonium chloride, tetraethyl ammonium bromide, tetrabutyl ammonium chloride, tetrabutyl ammonium bromide, trioctyl methylammonium chloride, benzyltrimethyl ammonium chloride, benzyltrimethyl ammonium bromide or phenyltrimethyl ammonium chloride, or a quaternary phosphonium salt such as tetrabutylphosphonium bromide or tetraphenylphosphonium bromide.

The phase transfer catalyst is used preferably in an amount of from 0.01 to 10 parts by weight, more preferably from 0.1 to 5 parts by weight, per 100 parts by weight of the primary alcohol and/or the secondary alcohol. If the amount of the phase transfer catalyst is large, the recovery of the product at the time of the post treatment tends to be low, and if it is small, the reaction rate tends to be low.

The reaction conditions in the case where the phase transfer catalyst is present, may be suitably modified depending upon the types and the amounts of the reactants. If the temperature is too low, the reaction will hardly proceed, and if it is too high, such is dangerous, and accordingly it is advisable to adjust the temperature to a level where the system is refluxed. Usually, the temperature is preferably from 40° to 80° C. The reaction pressure may be atmospheric pressure, reduced pressure or elevated pressure, preferably atmospheric pressure. The reaction time is usually from 1 to 10 hours.

The hydrofluorocarbon in the crude reaction products can be obtained as a high purity product by washing the crude reaction products with water or purifying it by distillation.

Further, it is possible to remarkably increase the total conversion of the iodofluorocarbon by conducting the above reaction in two steps using two reactors. Particularly, it is preferred to conduct the reaction in the following two steps using the alcohol mixture.

Namely, it is a method wherein the following two reaction steps are carried out by means of two reactors.

Reaction step 1: a step of reacting an iodofluorocarbon of the formula $I_nR_fI$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, with an alkali metal hydroxide under action of an alcohol mixture comprising of a primary alcohol and a secondary alcohol, to obtain a reduced product of the iodofluorocarbon, wherein the reduced product of the iodofluorocarbon is a mixture of $R_fI$ and $R_fH$, when n is 0, or a mixture of at least of two compounds selected from the group consisting of $IR_fI$, $HR_fI$ and $HR_fH$, when n is 1, and Reaction step 2: a step of reacting the reduced product of the iodofluorocarbon with an alkali metal hydroxide under action of an alcohol mixture comprising a primary alcohol and a secondary alcohol, to obtain a hydrofluorocarbon of the formula $H_nR_fH$ wherein n and $R_f$ are as defined above.

In reaction step 1, the above iodofluorocarbon is reacted with an alkali metal hydroxide under action of an alcohol mixture comprising a primary alcohol and a secondary alcohol. In reaction step 1, the alkali metal hydroxide may be used as it is or in the form of its aqueous solution. When it is used in the form of an aqueous solution, the alkali metal hydroxide is preferably in an amount of from 5 to 60 parts by weight, more preferably from 30 to 55 parts by weight, per 100 parts by weight of water. Particularly preferred is a saturated aqueous solution. Such an aqueous solution of an alkali metal hydroxide may be prepared, but it may be an inexpensive aqueous metal hydroxide solution commercially available for industrial use. In a case where the reaction is carried out in an industrial scale, it is very effective and advantageous also from the economical viewpoint to employ an inexpensive aqueous alkali metal hydroxide solution commercially available for industrial use. In reaction step 1, a phase transfer catalyst may be present. However, it is preferred that a phase transfer catalyst is not present, from the viewpoint of complication of the reactor, treatment of the waste catalyst and the cost for the reaction. Specific examples of the phase transfer catalyst may be the same as mentioned above.

If the reaction temperature for reaction step 1 is too low, the reaction will hardly proceed, and if it is too high, such is dangerous, and accordingly it is advisable to adjust the temperature to a level where the reaction solution is refluxed. The temperature is preferably from 40° to 70° C. The reaction pressure may be atmospheric pressure, reduced pressure or elevated pressure, and preferably atmospheric pressure. The reaction time is usually from 1 to 10 hours. The reaction may be carried out under pressure.

The reduced product of the iodofluorocarbon to be formed in reaction step 1 is a mixture of the iodofluorocarbon starting material and a compound with a structure wherein some or all of iodine atoms of the iodofluorocarbon starting material are substituted by hydrogen atoms.

For example, when the iodofluorocarbon starting material of the formula $I_nR_fI$ contains one iodine atom in its molecule (i.e. when n is 0), the reduced product of the iodofluorocarbon is a mixture of the starting material of the formula $R_fI$ and a hydrofluorocarbon of the formula $R_fH$ wherein the iodine atom in the iodofluorocarbon starting material is replaced by a hydrogen atom. Likewise, when the iodofluorocarbon starting material contains two iodine atoms in its molecule (i.e. when n is 1), the reduced product of the iodofluorocarbon is a mixture of at least two compounds selected from the group consisting of a compound of the formula $HR_fI$ (a partially reduced product) wherein one of the iodine atoms in the iodofluorocarbon starting material is replaced by a hydrogen atom, a hydrofluorocarbon of the formula $HR_fH$ wherein both iodine atoms are replaced by hydrogen atoms, and the starting material of the formula $IR_fI$ (although theoretically, it may be composed solely of the partially reduced product, it is usually a mixture). In the reduced product of the iodofluorocarbon, the reduction ratio=(mols of hydrogen atoms substituted for iodine atoms, contained in the reduced product of the iodofluorocarbon)/ (mols of iodine atoms contained in the molecules of the starting material) is preferably from 50 to 99%, more preferably from 60 to 95%, most preferably from 70 to 90%.

The reduced product of the iodofluorocarbon obtained in reaction step 1 can be made into a hydrofluorocarbon of a very high purity by reacting it in the same manner in reaction step 2.

Reaction step 2 is a step of reacting the reduced product of the iodofluorocarbon with an alkali metal hydroxide under action of an alcohol mixture comprising a primary alcohol and a secondary alcohol, to obtain a hydrofluorocarbon of the formula $H_nR_fH$, wherein n and $R_f$ are as defined above.

In a usual case, as the reduced product of the iodofluorocarbon in reduction step 2, the one obtained in the above reaction step 1 may be used as it is. However, it is usually preferred to employ the one having such treatment as washing with water is applied.

The alcohol mixture comprising the primary alcohol and the secondary alcohol, and the alkali metal hydroxide, used in reaction step 2, may be the same as or different from those used in reaction step 1.

From the viewpoint of the efficiency and economy, it is preferred to employ those used in reaction step 1 again or to incorporate a necessary compound to those used in reaction step 1. Further, if the reaction steps are repeated twice or more times, the alcohol mixture comprising the primary alcohol and the secondary alcohol, and the alkali metal hydroxide, used in the previous reaction step 2 may be reused in the next reaction step 1. Further, also in reaction step 2, the same phase transfer catalyst as used in reaction step 1, may be present.

The hydrofluorocarbon obtained in reaction step 2 may be washed with water to obtain a product of a high purity. If the reaction is carried out by repeating the steps twice, the total conversion of the iodofluorocarbon can further be increased. The purity of the hydrocarbon obtained, is usually at least 99.9%, preferably at least 99.99%. Accordingly, it can be used for various applications without purifying the product by distillation, except for a special application where even very small amount at a level of a few ppm of an iodine compound is required to be removed. Further, the reaction is highly selective, whereby the yield of the reaction is also very high.

In the present invention, an alkali metal alkoxide may be present at the time of reacting the iodofluorocarbon under action of the primary alcohol and the secondary alcohol. However, from the economical reason and in view of the handling efficiency, an alkali metal hydroxide is preferred to such an alkoxide.

The reaction in the presence of the alkali metal alkoxide, which is not necessarily clearly understood, may be represented by the following formula.

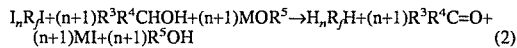
(2)

In the formula (2), $R_f$ and n are as defined above, $R^3$ is a hydrogen atom or an alkyl group, each of $R^4$ and $R^5$ is an alkyl group and M is an alkali metal atom.

When the alkali metal alkoxide is present, either one of the primary alcohol and the secondary alcohol may be employed. However, it is preferred to conduct the reaction under action of both the primary alcohol and the secondary alcohol.

Further, if water is contained in a large amount in the primary alcohol and the secondary alcohol, there will be such difficulties that the reaction system tends to separate into two layers, and the alkali metal alkoxide is likely to decompose. Therefore, the amount of water is preferably not larger than 300 ppm. Such an amount of water is not usually a problem, when a usual commercial reagent is employed. However, it is preferred to conduct dehydration treatment, as the case requires.

The amount of the primary alcohol and the secondary alcohol is usually from 0.1 to 10 parts by weight, preferably from 0.2 to 2 parts by weight, per part by weight of the hydrofluorocarbon starting material, either when they are used alone or when they are used in combination as a mixture. When they are used in combination as a mixture, their proportions are not particularly limited. In a usually case, however, the weight ratio of the primary alcohol to the secondary alcohol is preferably within a range of from 1000:1 to 0.5:1, more preferably within range of from 100:1 to 1:1.

The primary alcohol and/or the secondary alcohol is believed to serve as a hydrogen source for the hydrofluorocarbon. Further, an excess amount of the primary alcohol and/or the secondary alcohol is believed to serve as a solvent for the reaction. In the reaction, an alcohol compound (i.e. $R^5OH$ in the formula (2)) will be formed as a by-product, and such an alcohol compound is believed to serve as a hydrogen source for the hydrofluorocarbon or as a solvent again in the reaction system. In a usual case, as the alkali metal alkoxide, sodium methoxide, sodium ethoxide or potassium tertbutoxide is, for example, preferred.

The amount of the alkali metal alkoxide is usually preferably at least 1 mol per mol of iodine in the iodofluorocarbon starting metal, more preferably from 1 to 2 mols, from the viewpoint of the solubility to the system.

The reaction conditions in the case where the alkali metal alkoxide is present, may suitably be modified depending upon the types and the amounts of the reactants. If the temperature is too low, the reaction will hardly proceed, and if it is too high, such is dangerous, and it is advisable to adjust the temperature to a level where the system is refluxed. The temperature is usually preferably from 40° to 80° C. The reaction pressure may be atmospheric pressure, reduced pressure or elevated pressure, preferably atmospheric pressure. The reaction time is usually from 1 to 10 hours.

The hydrofluorocarbon in the crude reaction product may be purified to a product of a high purity by washing the crude reaction product with water or by purifying it by distillation.

According to the present invention, it is possible to obtain a hydrofluorocarbon with a high purity at an extremely high conversion when either method is employed. Further, the reaction of the present invention is excellent also in the reproducibility of the reaction performance.

The obtained hydrofluorocarbon is less likely to destroy the ozone layer as compared with the conventional chlorinated hydrocarbon or chlorinated fluorohydrocarbon. Thus, it is an excellent compound which can avoid unfavorable effects to environment. Further, it can be used also for conventional applications, for example, as a blowing agent, a cooling medium or a cleaning agent.

The present invention gives the very high conversion, whereby the amount of an unreacted hydrofluorocarbon remaining in the product can be minimized. Accordingly, the reaction can be conducted without coloring the polymer when the polymerization reaction is carried out by using a hydrofluorocarbon synthesized by the above method, as a solvent.

In such a case, the polymer is not particularly limited. However, the polymer is preferably a fluorine-type polymer such as a polytetrafluoroethylene, a copolymer of tetrafluoroethylene with a perfluoroalkyl vinyl ether, or a copolymer of tetrafluoroethylene with ethylene. Further, when the hydrofluorocarbon prepared by the present invention is used as a starting material for the preparation of e.g. a bromofluorocarbon, which is then used as a contrast medium or an artificial blood, it is advantageous that no phenomenon of coloring attributable to an iodine compound, is observed.

The functional mechanism of the alcohol mixture in the present invention is not clearly understood. However, it is believed that the primary alcohol and the secondary alcohol act on each other to accomplish the high conversion and high selectivity which can not be accomplished by the respective single uses and to provide an effect of suppressing formation of high boiling point compounds such as tar.

Now, the present invention will be described in further detail with reference Examples. However, it should be understood that the present invention is by no means restricted by such specific Examples.

EXAMPLE 1

Into a 1 l four-necked flask equipped with a stirrer, a reflux condenser, a dropping funnel and a thermometer, 256 g of methanol, 3 g of isopropyl alcohol and 46.4 g (1.16 mol) of sodium hydroxide were charged. The reactor was heated to bring the internal temperature to 60° C. Then, 223 g (0.5 mol) of $C_6F_{13}I$ was dropwise added thereto over a period of one hour. After completion of the dropwise addition, heating and refluxing were continued for 6 hours. The conversion was more than 99.9%. The reactor was cooled to room temperature, and then, 300 g of water was added to dissolve precipitated sodium iodide. The crude reaction solution was separated into two layers, and the fluorocarbon layer (lower layer) was further washed twice with 300 g of water to obtain 145 g (purity: 99.9%) of $C_6F_{13}H$. In the reactor, no formation of tar was observed.

EXAMPLE 2

Into 1 l four-necked flask equipped with stirrer, a reflux condenser, a dropping funnel and a thermometer, 256 g of methanol, 30 g of isopropyl alcohol, 74.3 g (1.13 mol) of 85% potassium hydroxide were charged. The reactor was heated to bring the internal temperature to 60° C. Then, 223 g (0.5 mol) of $C_6F_{13}I$ was dropwise added thereto over a period of one hour. After completion of the dropwise addition, heating and refluxing were continued for 5 hours. The conversion was more than 99.9%. The reactor was cooled to room temperature, and then, 300 g of water was added to dissolve precipitated potassium iodide. The crude reaction solution was separated into two layers, and the fluorocarbon layer (lower layer) was further washed with 300 g of water. The fluorocarbon layer was analyzed by gas chromatography, whereby the purity of $C_6F_{13}H$ was 99.5%, and no $C_6F_{13}I$ was detected. Obtained $C_6F_{13}H$ was 154 g. In the reactor, no formation of tar was observed.

EXAMPLE 3

Into a 20 l Hastelloy C autoclave equipped with a stirrer, a reflux condenser and a thermometer, 5130 g of methanol and 60 g of isopropyl alcohol and 1485 g (22.5 mols) of 85% potassium hydroxide were charged. The reactor was heated to bring the internal temperature to 50° C. Then, 4460 g (10 mols) of $C_6F_{13}I$ was fed thereto over a period of two hours. While maintaining the internal temperature of the reactor at a level of from 50° to 55° C., stirring was continued for 10 hours. The conversion was more than 99.9%. The reactor was cooled to room temperature, and then, 3200 g of water was added to dissolve precipitated potassium iodide. The crude reaction solution was separated into two layers, and the fluorocarbon layer (lower layer) was further washed twice with 3200 g of water to obtain 2975 g (purity: 99.9%) of $C_6F_{13}H$. In the reactor, no formation of tar was observed.

EXAMPLE 4

Into a 500 ml four-necked flask equipped with a stirrer, a reflux condenser, a dropping funnel and a thermometer, 256 g of methanol, 1.5 g of isopropyl alcohol and 74.3 g (1.13 mols) of 85% potassium hydroxide were charged. While maintaining the internal temperature of the reactor at a level of from 30° to 35° C., 113.5 g (0.25 mol) of $IC_4F_8I$ was dropwise added thereto over a period of two hours. After completion of the dropwise addition, stirring was continued at 35° C. for 3 hours. The conversion was more than 99.9%. The reactor was cooled to room temperature, and then, 300 g of water was added to dissolve precipitated potassium iodide. The crude reaction solution was separated into two layers, and the fluorocarbon layer (lower layer) was further washed with 300 g of water. The fluorocarbon layer was analyzed by gas chromatography, whereby the purity of $HC_4F_8H$ was 99.5%, and no $IC_4F_8I$ was detected. Obtained $HC_4F_8H$ was 39 g. In the reactor, no formation of tar was observed.

EXAMPLE 5

Into a 1 l four-necked flask equipped with a stirrer, a reflux condenser, a dropping funnel and a thermometer, 256 g of methanol, 3 g of isopropyl alcohol, and 74.3 g (1.13 mols) of 85% potassium hydroxide were charged. The reactor was heated to bring the internal temperature to 60° C. Then, 273 g (0.5 mol) of $C_8F_{17}I$ was dropwise added thereto over a period of one hour. After completion of the dropwise addition, heating and refluxing were continued for 8 hours. The conversion was more than 99.9%. The reactor was cooled to room temperature, and then, 300 g of water was added to dissolve precipitated potassium iodide. The crude reaction solution was separated into two layers, and the fluorocarbon layer (lower layer) was further washed with 300 g of water. The fluorocarbon layer was analyzed by gas chromatography, whereby the purity of $C_8F_{17}H$ was 99.6%, and no $C_8F_{17}I$ was detected. Obtained $C_8F_{17}H$ was 199 g. In the reactor, no formation of tar was observed.

EXAMPLE 6

Into a 20 l Hastelloy C autoclave equipped with a stirrer, a reflux condenser, a dropping funnel and a thermometer, 7700 g of methanol, 60 g of isopropyl alcohol and 1980 g (30 mols) of 85% potassium hydroxide were charged. The reactor was heated to bring the internal temperature to 55° C. Then, 4460 g (10 mols) of $C_6F_{13}I$ was fed thereto over a period of two hours. While maintaining the reactor at 55° C., stirring was continued for 10 hours. The conversion was more than 99.9%. Then, 3200 g of water was added to dissolve precipitated potassium iodide. The crude reaction solution was separated into two layers, and the fluorocarbon layer (lower layer) was further washed twice with 3200 g of water to obtain 2951 g of $C_6F_{13}H$ (purity: 99.9%, 3.9 ppm of $C_6F_{13}I$ was detected). In the reactor, no formation of tar was observed.

EXAMPLE 7

Into a 1 l four-necked flask equipped with a stirrer, a reflux condenser, a dropping funnel and a thermometer, 128 g of methanol, 64 g of isopropyl alcohol and 131 g (1.12 mols) of a 48% potassium hydroxide aqueous solution were charged. The reactor was heated to bring the internal temperature to 55° C. Then, 223 g (0.5 mol) of $C_6F_{13}I$ was dropwise added thereto over a period of one hour. After completion of the dropwise addition, the reaction was continued for 5 hours, whereupon the conversion was more than 99.9%. Further, in the reactor, there was no precipitation of potassium iodide. The reactor was cooled to room temperature. Then, 300 g of water was added to separate the crude reaction solution into two layers. The fluorocarbon layer (lower layer) was further washed three times with 300 g of water. The fluorocarbon layer was analyzed by gas chromatography, whereby the purity of $C_6F_{13}H$ was 99.5%, and no $C_6F_{13}I$ was detected. Obtained $C_6F_{13}H$ was 135 g. In the reactor, no formation of tar was observed.

EXAMPLE 8

Into a 1 l four necked flask equipped with a stirrer, a reflux condenser, a dropping funnel and a thermometer, 200 cc of methanol, 46.4 g (1.1 mols) of 97% sodium hydroxide and 5 g of tetrabutyl ammonium bromide were charged. The reactor was heated to bring the internal temperature to 60° C. Then, 223 g of (0.5 mol) of $C_6F_{13}I$ was dropwise added thereto over a period of one hour. After completion of the dropwise addition, heating and refluxing were continued for 5 hours. During this period, the internal temperature of the reactor was 57° C. The conversion at that time was 99.3%. The reactor was cooled to room temperature. Then, 200 g of water was added to dissolve precipitated potassium iodide. The crude reaction solution was separated into two layers, and the fluorocarbon layer (lower layer) was further washed with 300 g of water and dried over anhydrous magnesium sulfate. By distillation, 138 g (purity: 99.9%) of $C_6F_{13}H$ having a boiling point of 71° C., was obtained.

EXAMPLE 9

Into a 1 l four-necked flask equipped with a stirrer, a reflux condenser, a dropping funnel and a thermometer, 200 cc of methanol, 74.3 g (1.1 mols) of 85% potassium hydroxide and 1 g of tetrabutylphosphonium bromide were charged. The reactor was heated to bring the internal temperature to 60° C. Then, 223 g (0.5 mol) of $C_6F_{13}I$ was dropwise added thereto over a period of one hour. After completion of the dropwise addition, heating and refluxing were continued for tow hours. The conversion at that time was 98.1%. The heating and refluxing were further continued for two hours. Then, the reactor was cooled to room temperature, and 200 g of water was added to dissolve precipitated potassium iodide. The crude reaction solution was separated into two layers, and the fluorocarbon layer (lower layer) was further washed with 300 g of water to recover the fluorocarbon. Thus, 157 g of $C_6F_{13}H$ having a purity of 99.1%, was obtained.

EXAMPLE 10

Into a 1 l four-necked flask equipped with a stirrer, a distillation apparatus-equipped refluxing condenser, a dropping funnel and a thermometer, 200 cc of methanol, 131 g of (1.1 mols) of 48% potassium hydroxide and 3 g of tetrabutylphosphonium bromide were charged. The reactor was heated to bring the internal temperature to 60° C. Then, 223 g (0.5 mol) of $C_6F_{13}I$ was dropwise added thereto over a period of one hour. After completion of dropwise addition, heating and refluxing were continued for two hours. The conversion at that time was 97.0%. A fraction with a boiling point of up to 60° C. was recovered by distillation from the reactor. The recovered liquid was washed with 300 g of water to recover the fluorocarbon. Thus, 149 g of $C_6F_{13}H$ having a purity of 99.9%, was obtained.

EXAMPLE 11

Into a 1 l four-necked flask equipped with a stirrer, a distillation apparatus-equipped reflux condenser, a dropping funnel and a thermometer, 400 cc of isopropyl alcohol, 49.5 g (0.75 mol) of 85% potassium hydroxide and 1 g of tetrabutylphosphonium bromide were charged. The reactor was heated to bring the internal temperature to 60° C. Then, 223 g (0.5 mol) of $C_6F_{13}I$ was dropwise added thereto over a period of one hour. After completion of the dropwise addition, heating and refluxing were continued for one hour. The conversion at that time was 100%. A fraction with a boiling point of up to 75° C. was recovered by distillation from the reactor. The recovered liquid was washed five times with 200 g of water, and acetone and isopropyl alcohol were removed. Thus, 152 g of $C_6F_{13}H$ having a purity of 99.9%, was obtained.

EXAMPLE 12

Into a 1 l four-necked flask equipped with a stirrer, a distillation apparatus-equipped reflux condenser, a dropping funnel and a thermometer, 200 cc of isopropyl alcohol, 87.5 g (0.75 mol) of 48% potassium hydroxide and 1 g of tetrabutyl ammonium bromide were charged. The reactor was heated to bring the internal temperature to 60° C. Then, 223 g (0.5 mol) of $C_6F_{13}I$ was dropwise added thereto over a period of one hour. After completion of dropwise addition, heating and refluxing were continued for 3 hours. The conversion at that time was 99.9%. A fraction with a boiling point of up to 75° C. was recovered by distillation from the reactor. This recovered liquid was washed five times with 200 g of water, and acetone and isopropyl alcohol were removed. Thus, 146 g of $C_6F_{13}H$ having a purity of 99.9%, was obtained.

EXAMPLE 13

Into a 500 cc four-necked flask equipped with a stirrer, a distillation apparatus-equipped reflux condenser, a dropping funnel and a thermometer, 200 cc of methanol, 1.5 g of tetrabutyl ammonium bromide and 74.3 g (1.1 mols) of 85% potassium hydroxide were charged. While maintaining the internal temperature of the reactor at a level of from 30 to 35° C., 113.5 g (0.25 mol) of $IC_4F_8I$ was dropwise added thereto over a period of two hours. After completion of the dropwise addition, stirring was continued at 35° C. for 3 hours. Then, the temperature of the reactor was raised to 70° C., and the distillate was recovered. This liquid was washed with 100 g of ice water to recover a fluorocarbon. Thus, 42 g of $HC_4F_8H$ having a purity of 99.5%, was obtained.

EXAMPLE 14

Into a 1 l four-necked flask equipped with a stirrer, a reflux condenser, a dropping funnel and a thermometer, 250 cc of methanol and 3 g of tetrabutylphosphonium bromide and 74.3 g (1.1 mols) of 85% potassium hydroxide were charged. The reactor was heated to bring the internal temperature to 60° C. Then, 273 g (0.5 mol) of $C_8F_{17}I$ was dropwise added thereto over a period of one hour. After completion of the dropwise addition, heating and refluxing were continued for 8 hours. The conversion at that time was 99.6%. The reactor was cooled to room temperature. Then, 300 g of water was added to dissolve precipitated potassium iodide. The crude reaction solution was separated into two layers, and the fluorocarbon layer (lower layer) was further washed with 300 g of water to recover a fluorocarbon. Thus, 197 g of $C_8F_{17}H$ having a purity of 99.0%, was obtained.

EXAMPLE 15

Into a 1 l four-necked flask equipped with a stirrer, a reflux condenser, a dropping funnel and a thermometer, 200 cc of methanol and 10 cc isopropyl alcohol, 131 g (1.1 mols) of 48% potassium hydroxide and 5 g of tetrabutyl ammonium bromide were charged. The reactor was heated to bring the internal temperature to 60° C. Then, 223 g (0.5 mol) of $C_6F_{13}I$ was dropwise added thereto over a period of one hour. After completion of the dropwise addition, heating and refluxing were continued for two hours. During this period, the internal temperature of the reactor was 57° C. The conversion was 99.8%. The reactor was cooled to room temperature. Then, 100 g of water was added to dissolve precipitated potassium iodide. The crude reaction solution was separated into two layers, and the fluorocarbon layer (lower layer) was further washed 300 g of water and dried over anhydrous magnesium sulfate. By distillation, 42 g (purity: 99.0%) of $C_6F_{13}H$ having a boiling point of 71° C., was obtained.

EXAMPLE 16

Reaction step 1

Into a 10 l Hastelloy C autoclave equipped with a stirrer, a reflux condenser and a thermometer, 2400 g of methanol, 45 g of 2-propanol and 1970 g (16.88 mols) of a 48% potassium hydroxide aqueous solution were charged. The reactor was heated to bring the internal temperature to 60° C. Then, 3345 g (7.5 mols) of $F(CF_2)_6I$ was fed thereto over a period of 3 hours. While maintaining the internal temperature of the reactor at a level of from 60° to 63° C., stirring was continued for 5 hours. The conversion was 85.0%. The reactor was cooled to room temperature. Then, 2400 g of water was added to dissolve precipitated potassium iodide. The crude reaction solution was separated into two layers, and 2540 g of a fluorocarbon layer (lower layer) was obtained. The fluorocarbon layer contained 2040 g of $F(CF_2)_6H$ and 500 g of $F(CH_2)_6I$.

Reaction step 2

Into a 10 l Hastelloy C autoclave equipped with a stirrer, a reflux condenser and a thermometer, 2670 g of methanol, 50 g of 2-propanol, 2190 g (18.77 mols) of a 48% potassium hydroxide aqueous solution were charged. The reactor was heated to bring the internal temperature to 60° C. Then, 2540 g of the fluorocarbon layer obtained in Reaction step 1 was fed thereto over a period of one hour. While maintaining the internal temperature of the reactor at a level of from 60° to 63° C., stirring was continued for 5 hours. The conversion was 100.0%. The reactor was cooled to room temperature and then left to stand still to separate the solution into two layers. While retaining the upper layer in the reactor, the fluorocarbon layer (2430 g) of the lower layer was withdrawn. This liquid was washed twice with 2400 g of water, to obtain 2380 g of $F(CF_2)_6H$ having a purity of 99.95% containing no organic iodine compound.

EXAMPLE 17

Reaction step 1

The reactor in which the rest (the upper layer) left after withdrawing the fluorocarbon layer of the lower layer obtained in Reaction step 2 in Example 16, i.e. the mixture of methanol, 2-propanol and an aqueous potassium hydroxide solution, was remained, was heated to bring the internal temperature to 60° C. Then, 3345 g (7.5 mols) of $F(CF_2)_6I$ was fed thereto over a period of 3 hours. While maintaining the internal temperature of the reactor at a level of from 60° to 63° C., stirring was continued for 5 hours. The conversion was 85.2%. The reactor was cooled to room temperature. Then, 2400 g of water was added to dissolve precipitated potassium iodide. The crude reaction solution was separated into two layers, to obtain 2540 g of a fluorocarbon layer (lower layer). This liquid contained 2045 g of $C(CF_2)_6H$ and 495 g of $F(CF_2)_6I$.

Reaction step 2

Into a 10 l Hastelloy autoclave equipped with a stirrer, a reflux condenser and a thermometer, 2670 g methanol and 50 g of 2-propanol and 2190 g (18.77 mols) of a 48% potassium hydroxide aqueous solution were charged. The reactor was heated to bring the internal temperature to 60° C. Then, 2540 g of the fluorocarbon layer obtained in Reaction step 1 was fed thereto over a period of one hour. While maintaining the internal temperature of the reactor at a level of from 60° to 63° C., stirring was continued for 5 hours. The conversion was 100.0%. The reactor was cooled to room temperature and then left to stand still to separate the solution into two layers. While retaining the upper layer in the reactor, the fluorocarbon layer (2425 g) of the lower layer was withdrawn. This liquid was washed twice with 2400 g of water, to obtain 2375 g of $F(CF_2)_6H$ having a purity of 99.95% containing no organic iodine compound.

EXAMPLE 18

Into a 1 l four-necked flask equipped with a stirrer, a reflux condenser, dropping funnel and a thermometer, 400 cc of methanol (water content in the methanol being not higher than 200 ppm, the same is true in the following Examples) and 64.8 g (1.2 mols) of sodium methoxide were charged. The reactor was heated to bring the internal temperature to 65° C. Then, 446 g (1 mol) of $C_6F_{13}I$ was dropwise added thereto over a period of one hour. After completion of the dropwise addition, the reaction was continued for two hours, whereupon the internal temperature of the reactor was 57° C. The conversion was at least 99.9%. The reactor was cooled to room temperature. Then, 300 g of water was added to dissolve precipitated sodium iodide. The crude reaction solution was separated into two layers and the fluorocarbon layer (lower layer) was further washed with 300 g of water and dried over anhydrous magnesium sulfate. By distillation, 301 g (purity: 99.9%) of $C_6F_{13}H$ having a boiling point of 71° C., was obtained. In the reactor, no formation of tar was observed.

EXAMPLE 19

Into a 1 l four-necked flask equipped with a stirrer, a distillation apparatus-equipped reflux condenser, a dropping funnel and a thermometer, 400 cc of isopropyl alcohol (the water content in the isopropyl alcohol being not higher than 50 ppm, the same is true in the following Examples), and 84.2 g (0.75 mol) of potassium tertbutoxide were charged. The reactor was heated to bring the internal temperature to 60° C. Then, 223 g (0.5 mol) of $C_6F_{13}I$ was dropwise added thereto over a period of two hours. After completion of the dropwise addition, heating and refluxing were continued for one hour. The conversion at that time was 100%. A fraction with a boiling point of up to 75° C. was recovered by distillation from the reactor and further washed five times with 200 g of water, to obtain 151 g of $C_6F_{13}H$ having a purity of 99.8%. In the reactor, no formation of tar was observed.

EXAMPLE 20

Into a 500 cc four-necked flask equipped with a stirrer, a reflux condenser, a dropping funnel and a thermometer, 200 cc of methanol and 32.4 g (0.6 mol) of sodium methoxide were charged. While maintaining the internal temperature of the reactor at a level of from 30 to 35° C., 113.5 g (0.25 mol) of $IC_4F_8I$ was dropwise added thereto over a period of two hours. After completion of the dropwise addition, stirring was continued at 35° C. for 5 hours. The conversion at that time was 99.9%. The reactor was cooled to room temperature. Then, 300 g of water was added to dissolve precipitated sodium iodide. The crude reaction solution was separated into two layers, and the fluorocarbon layer (lower layer) was further washed with 100 g of water to obtain 43 g of $HC_4F_8H$ having a purity of 99.7%. In the reactor, no formation of tar was observed.

EXAMPLE 21

Into a 500 cc four-necked equipped with a stirrer, a reflux condenser, a dropping funnel and a thermometer, 200 cc of methanol and 32.4 g (0.6 mol) of sodium methoxide were charged. The reactor was heated to bring the internal temperature to 60° C. Then, 273 g of (0.5 mol) of $C_8F_{17}I$ was dropwise added thereto over a period of one hour. After completion of the dropwise addition, heating and refluxing were continued for 10 hours. The conversion at that time was 99.8%. The reactor was cooled to room temperature. Then, 300 g of water was added to dissolve precipitated potassium iodide. The crude reaction solution was separated into two layers, and the fluorocarbon layer (lower layer) was further washed with 300 g of water to obtain 201 g of $C_8F_{17}H$ having a purity of 99.4%. In the reactor, no formation of tar was observed.

EXAMPLE 22

Into a 1 l four-necked flask equipped with a stirrer, a reflux condenser, a dropping funnel and a thermometer, 200 cc of methanol, 10 cc of isopropyl alcohol and 32.4 g (0.6 mol) of sodium methoxide were charged. The reactor was heated to bring the internal temperature to 65° C. Then, 223 g (0.5 mol) of $C_6F_{13}I$ was dropwise added thereto over a period of one hour. After completion of the dropwise addition, the reaction was continued for two hours, whereupon the internal temperature of the reactor was 57° C. The conversion at that time was at least 99.9%. The reactor was cooled to room temperature. Then, 300 g of water was added to dissolve precipitated potassium iodide. The crude reaction solution was separated into two layers, and the fluorocarbon layer (lower layer) was further washed twice with 300 g of water and dried over anhydrous magnesium sulfate. By distillation, 149 g (purity: 99.9%) of $C_6F_{13}H$ having a boiling point of 71° C., was obtained. In the reactor, no formation of tar was observed.

COMPARATIVE EXAMPLE 1

Into a 1 l four-necked flask equipped with a stirrer, a reflux condenser, a dropping funnel and a thermometer, 510 g of methanol and 99 g (1.5 mols) of 85% potassium hydroxide were charged. The reactor was heated to bring the internal temperature to 65° C. Then, 446 g (1 mol) of $C_6F_{13}I$ was dropwise added thereto over a period of one hour. After completion of the dropwise addition, the reaction was continued for two hours, whereupon the internal temperature of the reactor was 60° C. The conversion was as low as 74%. Then, 300 g of water was added to the crude reaction solution to dissolve precipitated potassium iodide. Then, the solution was separated into two layers, and the fluorocarbon layer (lower layer) was further washed with 300 g of water. From the obtained fluorocarbon layer, a large amount of $C_6F_{13}I$ was detected.

COMPARATIVE EXAMPLE 2

Into a 1 l four-necked flask equipped with a stirrer, a distillation apparatus-equipped reflux condenser, a dropping funnel and a thermometer, 256 g of methanol and 131 g (1.12 mols) of a 48% potassium hydroxide aqueous solution were charged. The reactor was heated to bring the internal temperature to 55° C. Then, 223 g (0.5 mol) of $C_6F_{13}I$ was dropwise added thereto over a period of one hour. Further, heating and refluxing were continued for 5 hours, whereupon the conversion was 45.8%.

COMPARATIVE EXAMPLE 3

Into a 1 l four-necked flask equipped with a stirrer, a distillation apparatus-equipped reflux condenser, a dropping funnel and a thermometer, 510 g of isopropyl alcohol and 49.5 g (0.75 mol) of 85% potassium hydroxide were charged. The reactor was heated to bring the internal temperature to 65° C. Then, 223 g (0.5 mol) of $C_6F_{13}I$ was dropwise added thereto over a period of one hour. After completion of the dropwise addition, heating and refluxing were continued for one hour. The conversion was at least 99.9%, but in the reactor after recovering the distilled fraction by distillation of the crude reaction solution, a large amount of a black tar-like residue remained.

COMPARATIVE EXAMPLE 4

Reaction step 1

Into a 1 l four-necked flask equipped with a stirrer, a distillation apparatus-equipped reflux condenser, a dropping funnel and a thermometer, 256 g of methanol and 131 g (1.12 mols) of 48% of a potassium hydroxide aqueous solution were charged. The reactor was heated to bring the internal temperature to 55° C. Then, 223 g (0.5 mol) of $F(CF_2)_6I$ was dropwise added thereto over a period of one hour. Further, heating and refluxing were continued for 5 hours, whereupon the conversion was 45.8%. The reactor was cooled to room temperature. Then, 200 g of water was added to dissolve precipitated potassium iodide. The crude reaction solution was separated into two layers, to obtain 193 g of a fluorocarbon layer (lower layer).

Reaction step 2

Into a 1 l four-necked flask equipped with a stirrer, a distillation apparatus-equipped reflux condenser, a dropping funnel and a thermometer, 256 g of methanol and 131 g of a 48% potassium hydroxide aqueous solution were charged. The reactor was heated to bring the internal temperature to 55° C. Then, 193 g of the fluorocarbon layer obtained in Reaction step 1 was dropwise added thereto over a period of one hour. Further, heating and refluxing were continued for 5 hours. The reactor was cooled to room temperature and then left to stand still. The fluorocarbon of the lower layer was withdrawn and washed twice with 200 g of water. This liquid contained 88 g of $F(CF_2)_6H$ and 101 g of $F(CF_2)_6I$.

REFERENCE EXAMPLE 1

A stainless steel reactor having an internal capacity of 1.2 l, was deaerated, and 1200 g of $C_6F_{13}H$ prepared in Example 6 and 0.8 g of n-pentane as a chain transfer agent were charged, and 45 g of tetrafluoroethylene, 3.7 g of ethylene and 0.8 g of perfluorobutylethylene were charged. While maintaining the temperature at 65° C., 3 cc of a 1,1,2-trichloro-1,2,2-trifluoroethane solution containing 10 wt % of tert-butyl peroxyisobutyrate, was added as a polymerization initiator thereto, to initiate the reaction. During the reaction, a gas mixture of tetrafluoroethylene/ethylene (molar ratio: 53/47) was introduced, and the reaction pressure was maintained at 17.5 g/cm². Six hours later, 85 g of a white copolymer was obtained in the form of a slurry. The obtained polymer had a melting point of 270° C. and a heat decomposition initiating point of 340° C. The polymer was molded at 300° C., whereby a compression molded product was obtained without coloring. The product was maintained at 250° C. for 3 days, whereby no coloring was observed.

REFERENCE EXAMPLE 2

The crude reaction solution in Comparative Example 1 was distilled to obtain $C_6F_{13}H$ containing 200 ppm of $C_6F_{13}I$. Using this as a solvent for polymerization, polymerization was carried out in the same manner as in Reference Example 1. Ten hours later, 63 g of a white copolymer was obtained in the form of a slurry. This polymer had a melting point of 269° C. and a heat decomposition initiating point of 313° C. The polymer was molded at 300° C., whereby substantial coloring was observed.

According to the present invention, it is possible to produce a hydrofluorocarbon from an iodofluorocarbon at a high conversion and a high selectivity. Further, the present invention is safe and effective also from the viewpoint of the reaction conditions and thus is a method very advantageous from an industrial point of view.

In particular, according to the present invention, it is possible to obtain a hydrofluorocarbon of a high purity, and the method is excellent also in the reproducibility of the reaction performance. Further, the conversion of the starting material is very high, whereby it is possible to avoid various difficulties attributable to the unreacted iodofluorocarbon starting material and various iodine compounds formed from the iodofluorocarbon.

Further, as the alkali metal hydroxide, an aqueous solution of an inexpensive alkali metal hydroxide for industrial use, can be employed. When such an aqueous solution is employed, an alkali metal iodide will not precipitate, and thus, the method is advantageous also from the aspect of post-treatment, etc. Further, when the reaction is repeated, the reagent used in the first reaction can be re-used for the subsequent reaction, which is advantageous also from the viewpoint of the waste liquid treatment.

The obtained hydrofluorocarbon is a compound which is useful without presenting adverse effects to the ozone layer and can be used for an application such as a blowing agent, a cooling medium or a cleaning agent, as a substitute for a chlorofluorocarbon compound.

Especially when it is used as a solvent for polymerization, it is possible to prevent unnecessary broadening of the molecular weight distribution due to an iodofluorocarbon having a high chain transfer property or to prevent coloring of the polymerization product due to inclusion of an unreacted iodofluorocarbon.

What is claimed is:

1. A method for producing a hydrofluorocarbon of the formula a $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with an alkali metal hydroxide under action of an alcohol mixture comprising a primary alcohol and a secondary alcohol.

2. A method for producing a hydrofluorocarbon of the formula a $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with an alkali metal hydroxide under action of an alcohol mixture comprising a primary alcohol and a secondary alcohol in the presence of a phase transfer catalyst.

3. The method according to claim 1, wherein the alkali metal hydroxide is sodium hydroxide or potassium hydroxide.

4. The method according to claim 1, wherein the iodofluorocarbon is an iodofluorocarbon of the formula $I_nR_fI$ wherein n is 0 and $R_f$ is a $C_{3-8}$ linear or branched polyfluoroalkyl group, or an iodofluorocarbon of the formula $I_nR_fI$ wherein n is 1 and $R_f$ is a $C_{3-8}$ linear or branched polyfluoroalkylene group.

5. The method according to claim 1, wherein the primary alcohol is methanol.

6. The method according to claim 1, wherein the secondary alcohol is isopropyl alcohol.

7. The method according to claim 1, wherein the following two reaction steps are carried out by means of two reactors:

Reaction step 1: a step of reacting an iodofluorocarbon of the formula $I_nR_fI$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, with an alkali metal hydroxide under action of an alcohol mixture comprising of a primary alcohol and a secondary alcohol, to obtain a reduced product of the iodofluorocarbon, wherein the reduced product of the iodofluorocarbon is a mixture of $R_fI$ and $R_fH$, when n is 0, or a mixture of at least of two compounds selected from the group consisting of $IR_fI$, $HR_fI$ and $HR_fH$, when n is 1, and Reaction step 2: a step of reacting the reduced product of the iodofluorocarbon with an alkali metal hydroxide under action of an alcohol mixture comprising a primary alcohol and a secondary alcohol, to obtain a hydrofluorocarbon of the formula $H_nR_fH$ wherein n and $R_f$ are as defined above.

8. The method according to claim 2, wherein the phase transfer catalyst is a quaternary ammonium salt or a quaternary phosphonium salt.

9. A method for producing a hydrofluorocarbon of the formula $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with an alkali metal alkoxide under action of a primary alcohol and a secondary alcohol.

10. The method of claim 1, wherein said alcohol mixture comprises methanol and isopropyl alcohol.

11. The method of claim 1, wherein a ratio of said primary alcohol to said secondary alcohol is within a range of from 0.5:1 to 1,000:1.

12. The method of claim 1, wherein a ratio of said primary alcohol to said secondary alcohol is within a range of from 1:1 to 200:1.

13. The method of claim 1, wherein an amount of said primary alcohol is present in an amount of from 0.1–10 parts by weight per part by weight of said iodofluorocarbon.

14. The method of claim 1, wherein said alkali metal hydroxide is present in an amount of at least 1.5 moles per mole of iodofluorocarbon.

* * * * *